United States Patent
Sharpee et al.

(10) Patent No.: US 8,634,923 B2
(45) Date of Patent: Jan. 21, 2014

(54) CUSTOMIZATION OF IRREGULAR ARRAYS

(75) Inventors: Tatyana O. Sharpee, San Diego, CA (US); Charles F. Stevens, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 24 days.

(21) Appl. No.: 13/392,279

(22) PCT Filed: Aug. 25, 2010

(86) PCT No.: PCT/US2010/046699
§ 371 (c)(1),
(2), (4) Date: May 9, 2012

(87) PCT Pub. No.: WO2011/031498
PCT Pub. Date: Mar. 17, 2011

(65) Prior Publication Data
US 2012/0221076 A1     Aug. 30, 2012

Related U.S. Application Data

(60) Provisional application No. 61/236,829, filed on Aug. 25, 2009.

(51) Int. Cl.
*A61N 1/36* (2006.01)
*A61B 18/00* (2006.01)
*A61B 5/04* (2006.01)

(52) U.S. Cl.
USPC .............. 607/54; 607/53; 607/141; 600/383; 600/558; 382/155; 351/246

(58) Field of Classification Search
USPC ................... 351/246; 382/155; 600/383, 558; 607/53, 54, 141
See application file for complete search history.

(56) References Cited

U.S. PATENT DOCUMENTS 5,263,107 A * 11/1993 Ueda et al. ................... 382/157
6,400,989 B1 * 6/2002 Eckmiller ....................... 607/54
(Continued)

FOREIGN PATENT DOCUMENTS

WO    2077/128404 A1    11/2007
WO    2007/148038    12/2007

OTHER PUBLICATIONS

International Search Report and Written Opinion dated Mar. 22, 2011 for International Application No. PCT/US2010/046699, 6 pages.

(Continued)

*Primary Examiner* — Niketa Patel
*Assistant Examiner* — Christopher A Flory
(74) *Attorney, Agent, or Firm* — Kilpatrick Townsend and Stockton LLP

(57) ABSTRACT

An apparatus includes: an input configured to receive information indicative of sensed light locations; memory coupled to the input and storing indicia of receptive fields forming a mosaic, each of the receptive fields corresponding to an electrode, the mosaic including first and receptive fields having first and second shapes that are different, the memory further storing instructions; a processor coupled to the input and the memory and configured to read and execute the instructions to: analyze the information indicative of sensed light locations; determine, for each of respective ones of the sensed light locations, one or more receptive fields that include the corresponding sensed light location; and produce excitation indicia; the apparatus further including an output coupled to the processor and configured to be coupled to a retinal implant and to convey the excitation indicia toward the retinal implant.

23 Claims, 14 Drawing Sheets

(56) References Cited

U.S. PATENT DOCUMENTS

| | | | |
|---|---|---|---|
| 6,464,356 B1* | 10/2002 | Sabel et al. | 351/203 |
| 7,734,352 B2* | 6/2010 | Greenberg et al. | 607/53 |
| 2003/0158588 A1* | 8/2003 | Rizzo et al. | 607/54 |
| 2004/0030383 A1 | 2/2004 | Havey et al. | |
| 2008/0228242 A1* | 9/2008 | Fink et al. | 607/54 |
| 2008/0288021 A1 | 11/2008 | Schmid | |
| 2009/0312817 A1* | 12/2009 | Hogle et al. | 607/54 |
| 2010/0094382 A1* | 4/2010 | Pezaris et al. | 607/54 |
| 2010/0204754 A1* | 8/2010 | Gross et al. | 607/53 |
| 2010/0249878 A1* | 9/2010 | McMahon et al. | 607/54 |
| 2010/0256706 A1* | 10/2010 | Greenberg | 607/54 |

OTHER PUBLICATIONS

International Preliminary Report on Patentability and Written Opinion dated Feb. 28, 2012 for International Application No. PCT/US2010/046699, 4 pages.

* cited by examiner

CUSTOMIZATION OF IRREGULAR ARRAYS

CROSS-REFERENCES TO RELATED APPLICATIONS

This application is a national phase application of PCT Application No. PCT/US2010/046699, filed Aug. 25, 2010, entitled "CUSTOMIZATION OF IRREGULAR ARRAYS", which claims priority from U.S. Provisional Patent Application No. 61/236,829, filed Aug. 25, 2009, entitled "CUSTOMIZATION OF IRREGULAR ARRAYS," which are hereby incorporated by reference, as if set forth in full in this document, for all purposes.

STATEMENT AS TO RIGHTS TO INVENTIONS MADE UNDER FEDERALLY SPONSORED RESEARCH OR DEVELOPMENT

The U.S. Government has certain rights in this invention pursuant to Grant No. NIH K25MH068904 awarded by the National Institutes of Health.

BACKGROUND

In various applications, an irregular arrangement of sensors is used or available for sensing information and providing indicia of this information. The irregularity of the arrangement can significantly decrease the accuracy of the representation of a particular stimulus. This is especially true when using a regularly-disposed arrangement of exciters to excite the irregularly-arranged sensors.

For example, functional retinal ganglion cell sensors are irregularly arranged in persons, especially those with retinal degradation who have lost most or all of their photoreceptor cells. Such loss may occur as a result of age-related macular degeneration or retinitis pigmentosa, which together cause blindness in millions of people worldwide. In such cases, even though photoreceptor cells are lost, about 30% of retinal ganglion cells survive, and these cells are still capable of relaying signals to the brain. The surviving ganglion cells actively migrate and form anomalously re-wired circuits. This re-wiring causes unavoidable irregularities at the retina-brain interface because it is not known a priori how electrical pulses on a given portion of the retina will be perceived by the brain.

Retinal prosthetic devices hold great promise in restoring partial vision to blind patients who have lost their photoreceptor cells. Retinal implants utilize a video camera as a replacement for photoreceptors transducing light patterns, and an array of electrodes positioned on the retina to deliver electrical signals based on the camera output to the retinal ganglion cells. Due to the ganglion cell irregularity, light sensed by the camera at a particular location in a field of view that is translated into a corresponding signal for an electrode at a similar relative position in the retinal implant may not be perceived by the person as light emanating from the particular location in the field of view, but from a different location.

SUMMARY

An example of apparatus according to the disclosure for use in a retinal implant imaging system includes: an input configured to receive information indicative of sensed light locations; memory communicatively coupled to the input and storing indicia of receptive fields forming a mosaic, each of the receptive fields corresponding to an electrode to be excited if the information indicative of sensed light indicates sensed light in the receptive field, the mosaic including a first receptive field having a first shape and a second receptive field having a second shape that is different from the first shape, the memory further storing processor-readable, processor-executable instructions; a processor communicatively coupled to the input and the memory and configured to read and execute the instructions to: analyze the information indicative of sensed light locations; determine, for each of respective ones of the sensed light locations, one or more receptive fields that include the corresponding sensed light location; and produce excitation indicia corresponding to the receptive field determined to include a sensed light location; and an output communicatively coupled to the processor and configured to be communicatively coupled to the retinal implant and to convey the excitation indicia toward the retinal implant.

Implementations of such an apparatus may include one or more of the following features. The receptive fields are irregularly-shaped and irregularly-disposed within the mosaic. The instructions configured to be read and executed by the processor to determine the one or more receptive fields are associated with a particular patient. The instructions configured to be read and executed by the processor to determine the one or more receptive fields that include the corresponding sensed light location are configured such that the processor will map the sensed light locations to the one or more respective fields according to a mapping associated with the particular patient. The first receptive field has a largest area of the receptive fields of the mosaic and the second receptive field has a smallest area of the receptive fields of the mosaic, and the area of the first receptive field is greater than 50% larger than the area of the second receptive field. The mosaic includes at least 12 receptive fields. The receptive fields are differently-shaped. The mosaic includes at least 50 differently-shaped receptive fields.

An example of method according to the disclosure of configuring an apparatus for use in a retinal implant system for a user includes: exciting electrodes of a retinal implant of the retinal implant system, the retinal implant disposed on a retina of the user, the electrodes being excited individually to produce a perception in the user of a spot of light for each electrode; prompting the user to provide, and receiving from the user, indicia of perceived locations of the spots of light; setting initial receptive fields disposed about the perceived locations, the initial receptive fields forming an initial mosaic; and storing mosaic configuration information in the apparatus, the stored mosaic configuration information being indicative of receptive field configurations disposed about the perceived locations and associating each receptive field with locations in a field of view of the user corresponding to the retinal implant.

Implementations of such a method may include one or more of the following features. The method may further include: altering configurations of the initial receptive fields to produce a plurality of altered mosaic configurations comprising altered receptive fields; and determining mutual information of each of the mosaic configurations; where storing the mosaic configuration information comprises storing the altered mosaic configuration with a highest mutual information value of the altered mosaic configurations. The method may further include: determining a baseline mutual information value of the initial mosaic with the initial receptive fields; determining a new mutual information value for each altered mosaic; and replacing the baseline mutual information value with the new mutual information value if the new mutual information value is greater than the baseline mutual information value; where the storing comprises storing the mosaic configuration information of the altered mosaic configuration corresponding to the baseline mutual information once new mutual information values for all desired altered mosaic configurations have been determined and compared with the baseline mutual information value as of the time when the respective new mutual information values are determined.

Determining the new mutual information includes calculating areas of only receptive field area portions whose areas change with respect to a previous mosaic configuration, each of the receptive field area portions being associated with a unique set of one or more of the electrodes. The method may further include repeatedly altering the configuration of each of the altered receptive fields. The altering includes: selecting a first receptive field of the initial receptive fields; altering the configuration of the first receptive field using each of a first predetermined set of configuration parameter values to produce a first altered receptive field; and performing the selecting and altering for a second receptive field of the initial receptive fields, using a second predetermined set of configuration parameter values, after each of the first predetermined set of configuration parameter values have been used to alter the configuration of the first receptive field. The selecting and altering are performed for each of the initial receptive fields to determine a set of altered receptive fields. The method may further include performing the selecting and altering for each of the altered receptive fields of the set of altered receptive fields a predetermined number of times to determine a corresponding predetermined number of sets of altered receptive fields. Altering configurations of the initial receptive fields to produce a plurality of altered mosaic configurations includes altering a first receptive field of the initial receptive fields and altering at least a second receptive field adjacent to the first receptive field to produce a first altered mosaic configuration, and determining mutual information of each of the mosaic configurations includes, for the first altered mosaic configuration: determining an altered mutual information contribution of only receptive field area portions whose areas change with respect to a previous mosaic configuration, each of the receptive field area portions being associated with a unique set of one or more of the electrodes; and modifying an initial mutual information value of the initial mosaic by replacing an initial mutual information contribution of initial receptive field area portions associated with altered receptive field area portions with the altered mutual information contribution. The setting includes setting initial ellipses of particular sizes, aspect ratios, and orientations, and the altering includes changing the sizes, aspect ratios, and orientations of each of the initial ellipses. The altering includes changing one of the size, aspect ratio, or orientation of a selected receptive field to form each altered mosaic. The altering includes changing a perimeter of a selected receptive field to be different than a perimeter of another of the receptive fields. The altering further includes changing a perimeter of a selected receptive field in accordance with a Legendre polynomial. Changing the perimeter of the selected receptive field includes changing coefficients of the Legendre polynomial. The setting, storing, altering, and determining are done without receiving user input beyond the indicia of perceived locations of the spots of light, and outside the presence of the user.

An example of computer program product, according to the disclosure, resides on a computer-readable medium and includes computer-readable non-transitory instructions configured to cause a computer to: set initial receptive fields disposed about perceived locations, the initial receptive fields forming an initial mosaic, the perceived locations being indicative of locations of perceived light by a user in response to stimulation of portions of a retinal implant disposed on a retina of the user; and alter configurations of the initial receptive fields to produce a plurality of altered mosaic configurations comprising altered receptive fields; determine mutual information of each of the mosaic configurations; and store mosaic configuration information, the stored mosaic configuration information being indicative of receptive field configurations disposed about the perceived locations and associating each receptive field with locations in a field of view of the user corresponding to the retinal implant, the stored mosaic configuration information being indicative of the mosaic configuration with a highest mutual information value of the altered mosaic configurations.

Implementations of such a computer program product may include one or more of the following features. The instructions configured to cause the computer to determine the mutual information are configured to cause the computer to calculate areas of only receptive field area portions whose areas change with respect to a previous mosaic configuration, each of the receptive field area portions being associated with a unique set of one or more of the electrodes. The instructions configured to cause the computer to alter configurations are configured to cause the computer to: select a first receptive field of the initial receptive fields; alter the configuration of the first receptive field using each of a first predetermined set of configuration parameter values to produce a first altered receptive field; and select and alter a second receptive field of the initial receptive fields, using a second predetermined set of configuration parameter values, after each of the first predetermined set of configuration parameter values have been used to alter the configuration of the first receptive field. The instructions configured to cause the computer to alter configurations of the initial receptive fields to produce a plurality of altered mosaic configurations are configured to cause the computer to alter a first receptive field of the initial receptive fields and altering at least a second receptive field adjacent to the first receptive field to produce a first altered mosaic configuration, and wherein the instructions configured to cause the computer to determine mutual information of each of the mosaic configurations are configured to cause the computer to, for the first altered mosaic configuration: determine an altered mutual information contribution of only receptive field area portions whose areas change with respect to a previous mosaic configuration, each of the receptive field area portions being associated with a unique set of one or more of the electrodes; and modify an initial mutual information value of the initial mosaic by replacing an initial mutual information contribution of initial receptive field area portions associated with altered receptive field area portions with the altered mutual information contribution.

Also, or alternatively, implementations of the example computer program product may include one or more of the following features. The instructions configured to cause the computer to set are configured to cause the computer to set initial ellipses of particular sizes, aspect ratios, and orientations, and the instructions configured to cause the computer to alter are configured to cause the computer to change the sizes, aspect ratios, and orientations of each of the initial ellipses. The instructions configured to cause the computer to alter are configured to cause the computer to change one of the size, aspect ratio, or orientation of a selected receptive field to form each altered mosaic. The instructions configured to cause the computer to alter are configured to cause the computer to change a perimeter of a selected receptive field to be different than a perimeter of another of the receptive fields. The instructions configured to cause the computer to alter are configured to cause the computer to change a perimeter of a selected receptive field in accordance with a Legendre polynomial.

Techniques described herein may provide one or more of the following capabilities. Resolution of information reproduced from irregularly-arranged sensors can be improved. For example, spatial resolution of images reproduced by a human brain from input from irregularly-arranged retinal ganglion cells stimulated by regularly-arranged retinal implant electrodes can be improved. Error-correcting code performance can be improved by adjusting one or more parameters to accommodate irregularities, e.g., patient-specific irregularities, in signal transmission.

DETAILED DESCRIPTION

Embodiments of the disclosure provide techniques for use in retinal implant systems and for programming retinal implant systems. For example, patient-specific data are collected from patient response to retinal implant stimuli. The patient-specific data are used to determine positions of percepts corresponding to retinal implant exciters (e.g., electrodes). Shapes of the receptive fields are varied and mutual Shannon information is determined for each variation. The shapes are varied to attempt to increase the mutual Shannon information of the combined receptive fields. A set of receptive fields are determined based on analysis of the mutual Shannon information and the set is programmed into a translation portion of a retinal implant system. The retinal implant system includes a camera, the retinal implant with a grid of electrodes, and the translation portion communicatively connected to the camera and the retinal implant. The translation portion receives indications of light detected at portions of a field of view of the camera and translates these into excitations of the electrodes using the determined set of receptive fields that maps the field of view of the user of the system to the electrode grid. Other embodiments are within the scope of the disclosure and claims.

Figure 1:
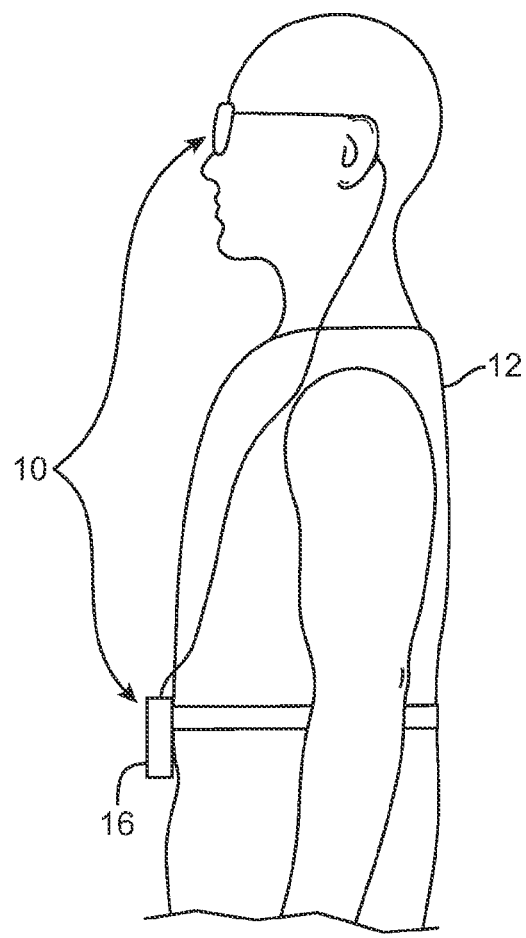
FIG. 1 shows a sensor adaptation system, here a retinal-implant system.
Figure 2:
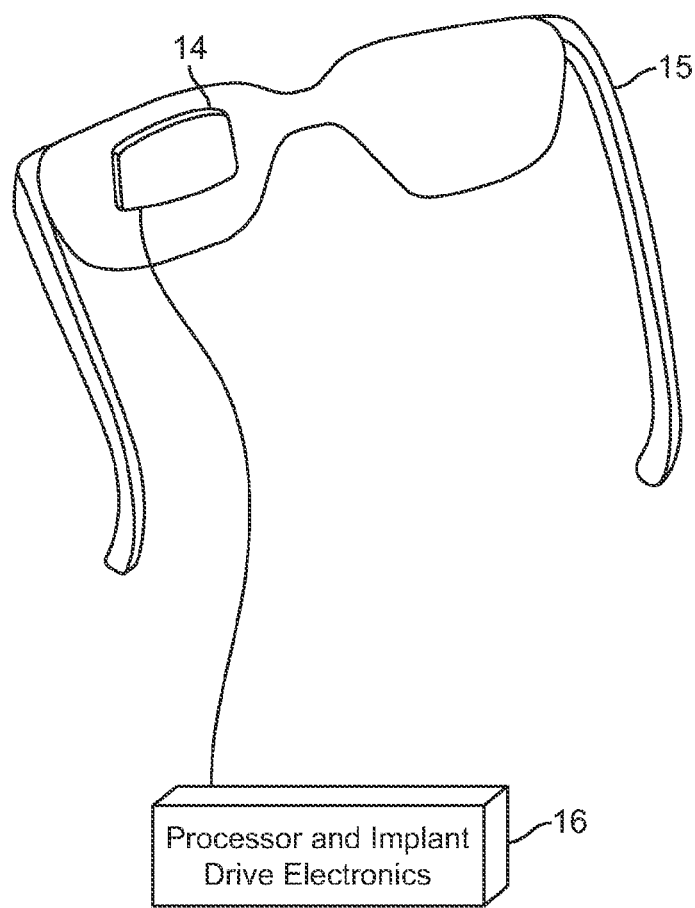
FIG. 2 is a perspective view of a camera and electronics pack of the system shown in FIG. 1.
Figure 3:
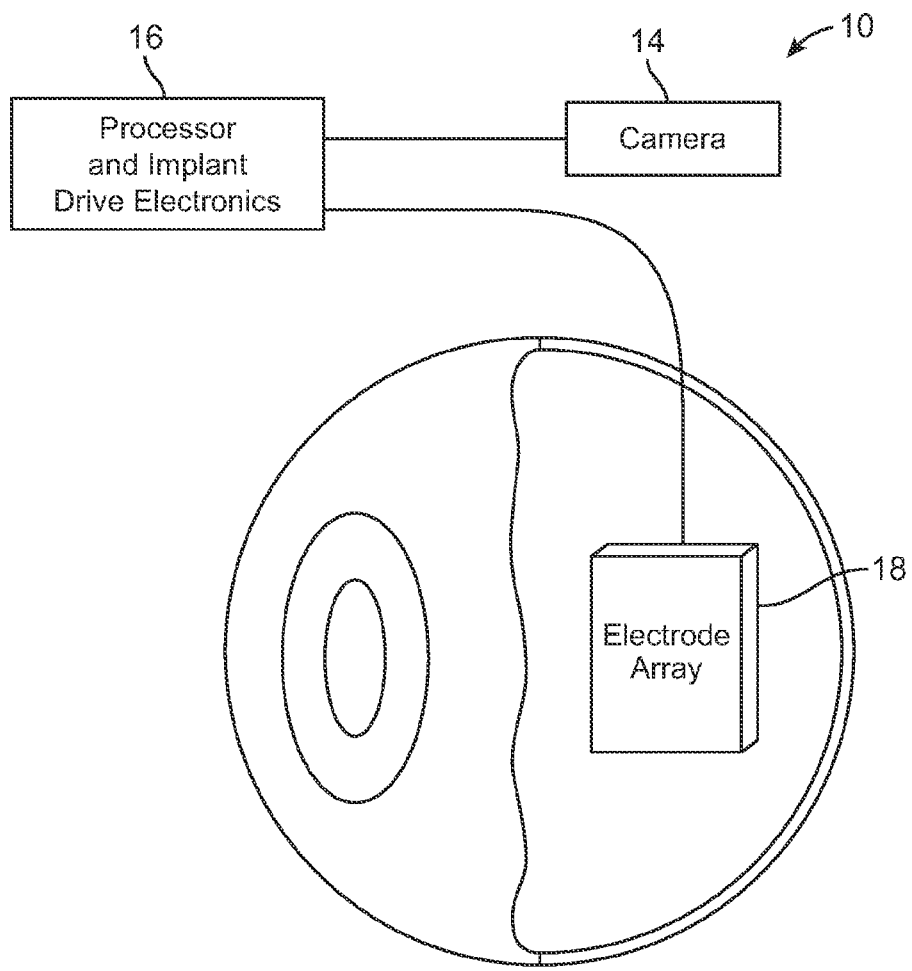
FIG. 3 is a block diagram and partially-cut-away view of components of the system shown in FIG. 1.

Referring to FIGS. 1-3, an irregularly-arranged-sensor adaptation system 10 is worn by a user 12. The system 10 includes a sensor 14, a combined processor and implant drive electronics pack 16, and an excitation array 18. Here, the system 10 is a retinal implant system, the sensor 14 is a camera, and the excitation array 18 is a retinal implant electrode array. The system 10 is configured to be worn by the user 12 to sense visual stimuli in the vicinity of the user 12, to translate this information into stimuli for the electrode array 18 adapted for the irregular arrangement of functional retinal ganglion cells in the user 12. The camera 14 is mounted to glasses 15 and configured to receive visual information and translate this into signals that the camera 14 sends to the electronics pack 16. The electronics pack 16 is wired to the camera 14 for receiving the signals representative of visual stimuli, and is configured to be portable, being conveniently worn or held by the user 12. The electronics pack 16 is further configured to translate the signals received by the camera 14 into stimuli for the array 18, as described further below, in order to provide stimuli for the user's retinal ganglion cells such that the user's brain can process the array stimuli to form visual information. The electronics pack 16 is wired to the electrode array implant 18 to deliver signals to drive electrodes in the array 18. While in the system 10 the camera 14 is wired to the pack 16 and the pack 16 is wired to the array 18, one or both of these connections could be wireless. Further, while the system 10 is shown as having a single camera 14 and a single retinal implant 18, other configurations are possible, such as a camera and a corresponding retinal implant for each eye.

Figure 4:
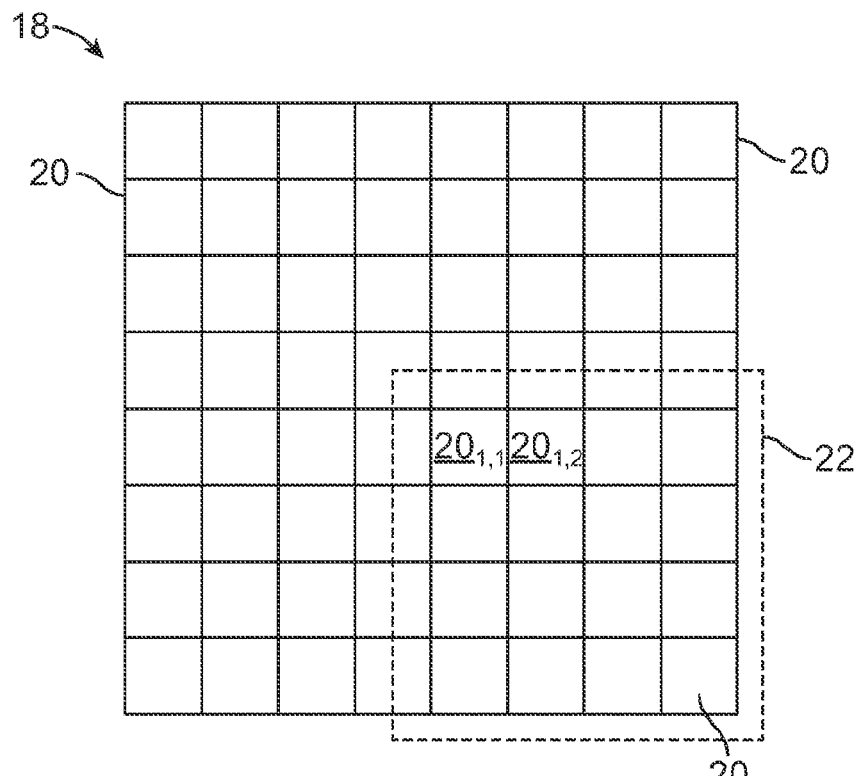
FIG. 4 is a block diagram of an electrode grid of an electrode array shown in FIG. 3.
Figure 5:
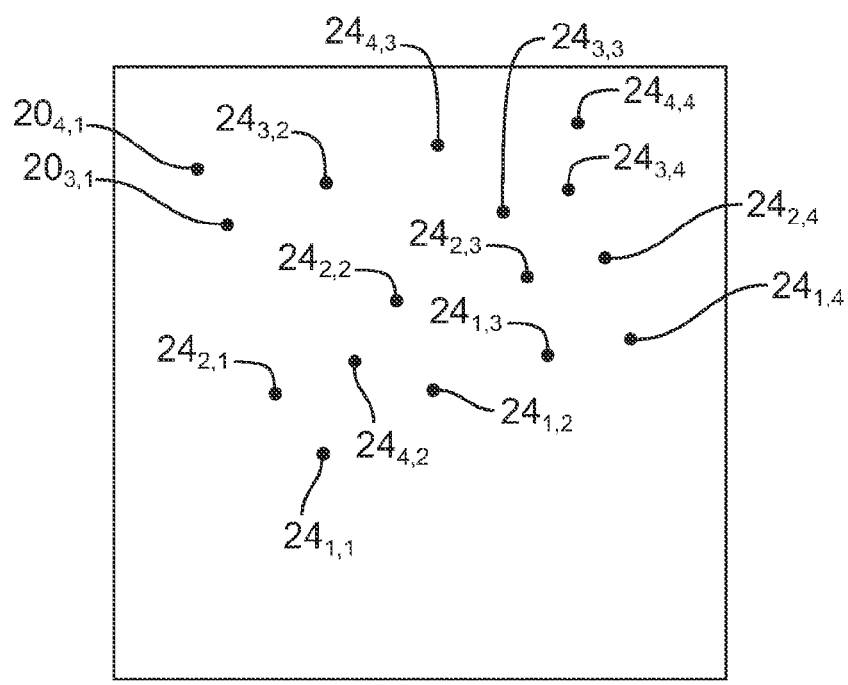
FIG. 5 is a graph of perceived locations of light corresponding to a portion of the electrode grid shown in FIG. 4.

Referring also to FIGS. 4-5, the electrode array 18 includes a set of regularly-spaced electrodes 20 that map to an irregular, although semi-regular, set of round spots of light perceived by the user 12. Here, the array 18 includes many electrodes 20, e.g., at least 12, 16, or 50 and here 64 electrodes 20 arranged in an 8×8 grid. When each of the electrodes 20 is stimulated, the user 12 perceives a round spot of light. The location of the perceived spots of light correspond to the stimulated electrodes, but the relative positions of the perceived spots do not correspond exactly with the layout of the electrodes 20. For example, as shown in FIG. 5, a 4×4 subset 22 of the electrodes $20_{1,1}, 20_{1,2}, \ldots 20_{4,4}$ may produce a set of perceived spots of light 24 that are disposed in an irregular, although semi-regular, manner. The system 10 is configured to adapt the excitations of the electrodes 20 in accordance with the perception of the user 12 that reflects the connections of the user's ganglion cells and the translation from light incident upon the user's retina to the perception of the incident light as interpreted by the user's brain from signals from the ganglion cells.

Figure 6:
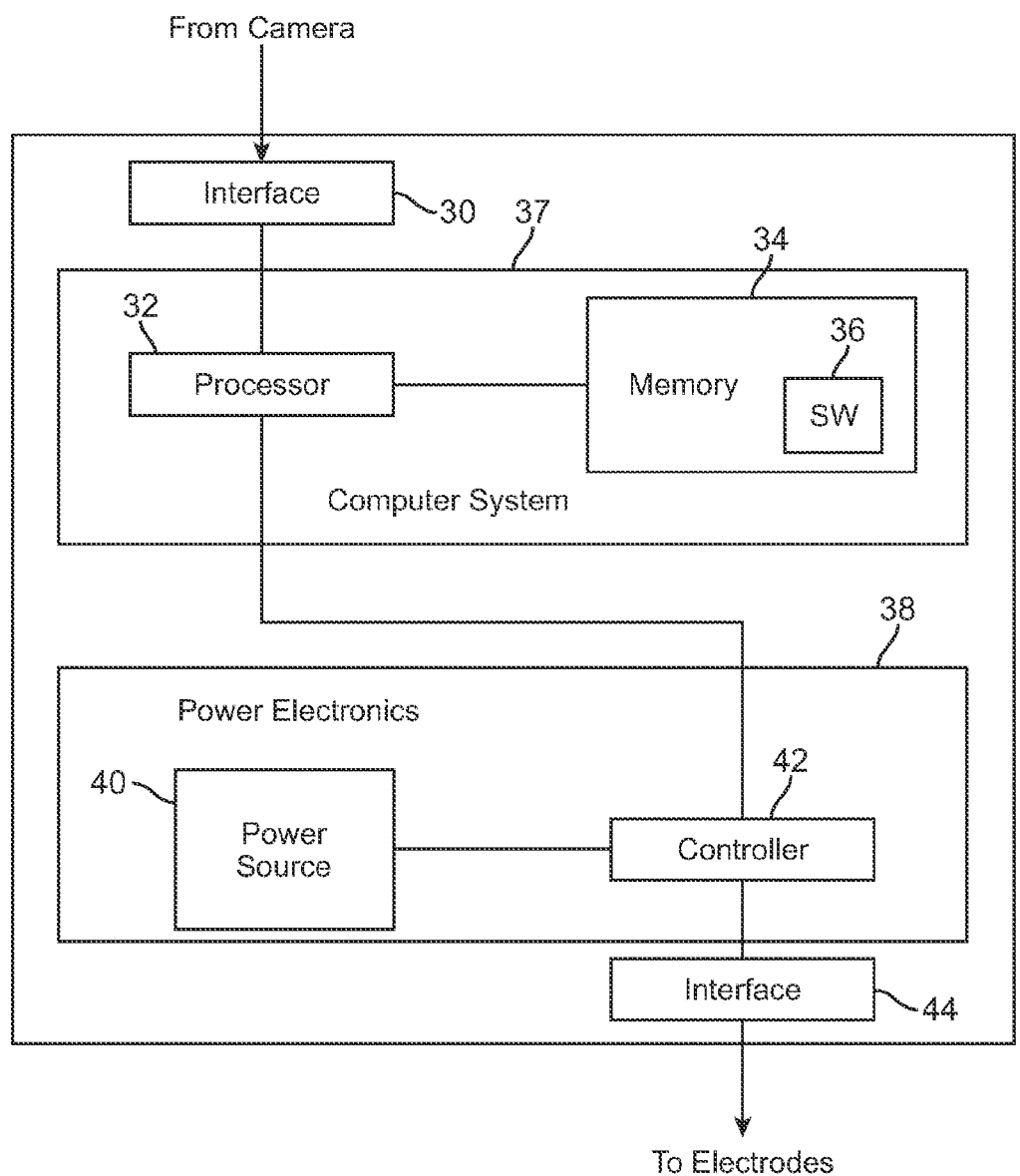
FIG. 6 is a block diagram of the electronics pack shown in FIG. 1.

Referring to FIG. 6, the electronics pack 16 includes interfaces 30, 44, a computer system 37, and power electronics 38. The interface 30 is configured to be connected to the camera 14 and to receive information from the camera 14 indicative of sensed light. The computer system 37 includes a processor 32 and memory 34. The processor 32 is preferably an intelligent device, e.g., a personal computer central processing unit (CPU) such as those made by Intel® Corporation or AMD®, a microcontroller, an application specific integrated circuit (ASIC), etc. The memory 34 is connected to the processor 32 and includes random access memory (RAM) and read-only memory (ROM). The computer system can store, e.g., in the memory 34, computer-readable, computer-executable non-transitory software (SW) code 36 containing instructions for controlling the processor 32 to perform functions described below (although the description may read that the software 36 performs the function(s)). The software 36 can be loaded onto the pack 16 by being downloaded via a network connection, uploaded from a disk, etc. The processor 32 is connected to the power electronics 38 that includes a power source 40, e.g., a battery, and an output controller 42. The processor 32 is configured to cause the output controller 42 to selectively connect the power source 40 to the electrodes 20 to selectively power the electrodes 20 and thus selectively stimulate the user's ganglion cells to induce visual perception. The controller 42 is connected, configured to provide power, to the interface 44 that is configured to provide power on individual lines directly connected to the electrodes 20. The controller 42 and interface could, however, be configured to provide one power signal and also provide instructions for a multiplexer of the array 18 to control distribution of the power to individual electrodes 20.

Figure 7:
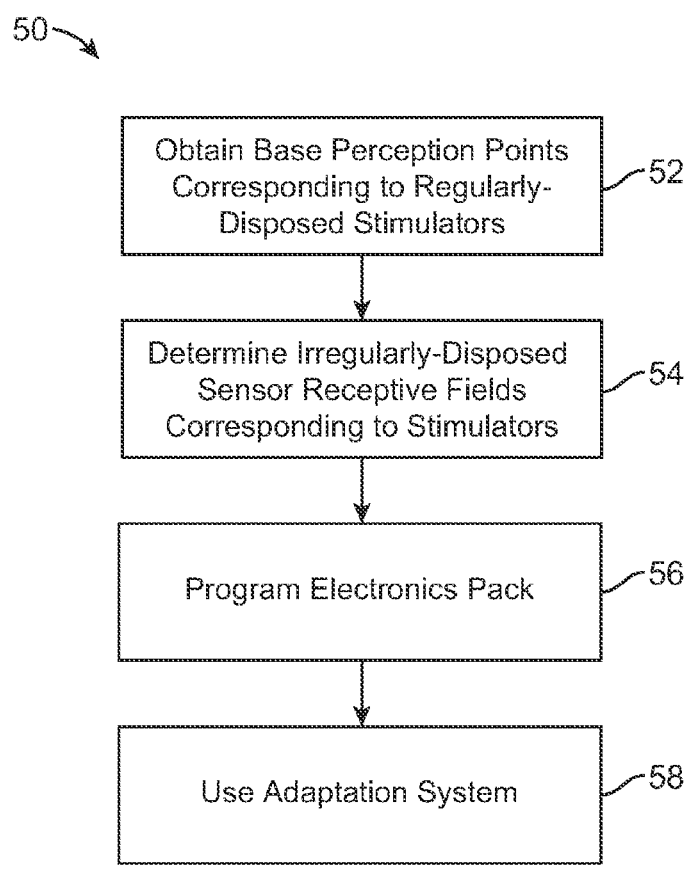
FIG. 7 is a block flow diagram of a process of configuring and using the system shown in FIG. 1.

Referring to FIG. 7, with further reference to FIGS. 1-6, a process 50 of configuring and using the system 10 includes the stages shown. The process 50 is, however, exemplary only and not limiting, as the process 50 can be altered from the specifics shown and described. At stage 52, base perception points 24 are obtained for regularly-disposed stimulators, here for the user 12 corresponding to the array electrodes 20 of the implant 18 in the user 12. At stage 54, the base perception points 24 are used to determine irregularly-disposed sensor receptive fields corresponding to the stimulators, here retinal ganglion cell receptive fields (RFs) corresponding to the array electrodes 20. The receptive fields may represent a filter, e.g., a linear filter, that when applied to incoming visual patterns will determine, for each electrode 20 of the array 18, whether or not to activate the electrode 18. At stage 56, the RFs are programmed into the electronics converter pack, here the ganglion cell RFs being programmed into the electronics pack 16, i.e., the memory 34. At stage 58, the adaptation system is used, here the system 10 being used by the user 12 to produce perceived visual data in response to visual information received by the camera 14. Stages 54 and 56 are preferably done off-line, outside the presence of the user 12 and without input from the user beyond that received in stage 52. Thus, stages 54 and 56 can be performed thoroughly, over a significant period of time, e.g., hours, days, or even weeks.

Figure 8:
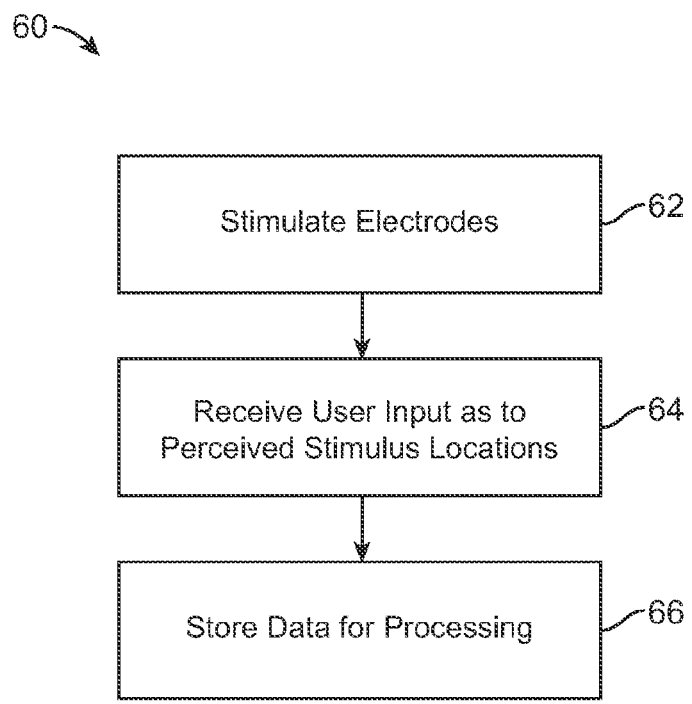
FIG. 8 is a block flow diagram of a portion of the process shown in FIG. 7.
Figure 9:
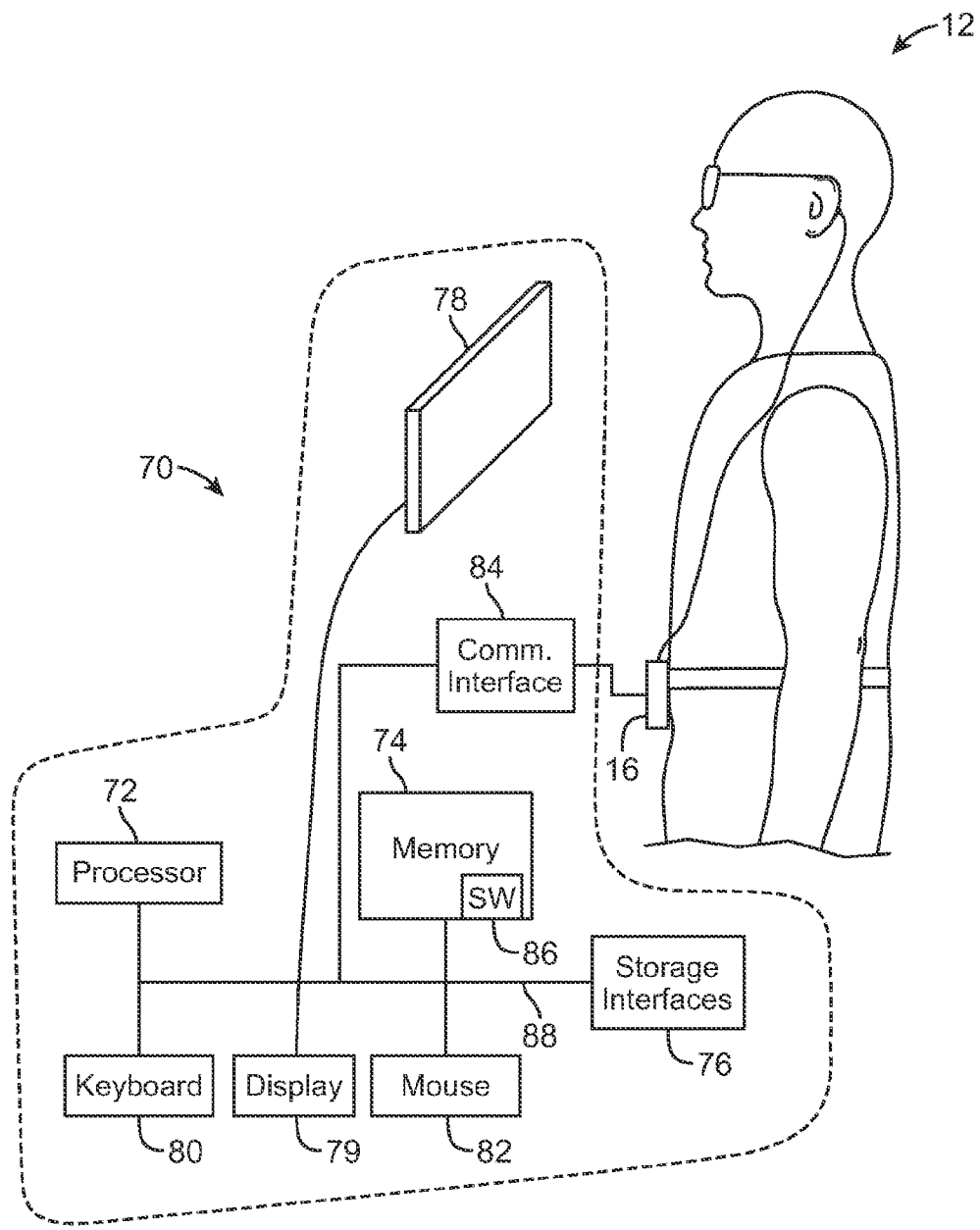
FIG. 9 is a block diagram of a system for programming the electronics pack shown in FIG. 1.

Referring to FIGS. 8-9, with further reference to FIGS. 1-7, the stage 52 of the process 50 comprises a process 60 that includes the stages shown. The process 60 is, however, exemplary only and not limiting, as the process 60 can be altered from the specifics shown and described.

During the process 60, the user interacts with a computer system 70 including a processor 72, memory 74, storage interfaces 76, an input device 78, a display 79, a keyboard 80, a mouse 82, and a communications interface 84. The processor 72 is preferably an intelligent device, e.g., a personal computer central processing unit (CPU) such as those made by Intel® Corporation or AMD®, a microcontroller, an application specific integrated circuit (ASIC), etc. The memory 74 includes random access memory (RAM) and read-only memory (ROM). The storage interfaces 76 comprise mechanisms for interacting with storage devices to read data from and/or store data to the storage devices. For example, the interfaces 76 may include disk drives (e.g., hard-disk drive, floppy-disk drives, a CD-ROM drive, and/or a zip drive), USB drives, etc. The input device 78 is a touch-sensitive screen that the user 12 can actuate to indicate relative locations of the perceived spots of light 24. Other forms of input devices, however, may be used. The display 79 is a cathode-ray tube (CRT), although other forms of displays are acceptable, e.g., liquid-crystal displays (LCD) including TFT displays. The keyboard 40 and mouse 42 provide data input mechanisms for an operator (not shown) of the computer system 70. The system 70 can store, e.g., in the memory 74, computer-readable, computer-executable software code 86 containing instructions for controlling the processor 72 to perform functions described below (although the description may read that the software 86 performs the function(s)). The software 86 can be loaded onto the memory 74 by being downloaded via a network connection, uploaded from a disk, etc. The processor 72, the memory 74, the interfaces 76, the input device 78, the display 79, the keyboard 80, the mouse 82, and the interface 84 are connected for bi-directional communication by a bus 88. Further, the processor 72 is connected via the interface 84 to the electronics pack 16.

At stage 62 of the process 60, the electrodes 20 of the array 18 are stimulated. The operator of the system 70 controls the processor 72 (e.g., using the keyboard 80 and/or the mouse 82) via the software 84 and the interface 86 to cause the pack 16 to cause the electrodes 20 in the implant 18 to be stimulated one at a time. The stimulated electrodes 20 cause the user 12 to perceive the corresponding spots of light 24.

At stage 64, the user 12 indicates locations of where the user 12 perceives the spots of light 24. The input device 78 is placed in front of the user 12, with the user's head fixed and the device 78 in what would be the user's field of view. The user 12 touches the input device 78 at locations corresponding to the locations of the perceived light spots 24 produced by the excited electrodes 20.

At stage 66, the location data of the perceived spots of light 24 are stored for processing. The input device 78 relays indicia of the locations indicated by the user 12 to the processor 72. The processor 72 stores the locations in the memory 74 for use by the processor 72 as discussed below regarding stage 54 of the process 50.

Figure 10:
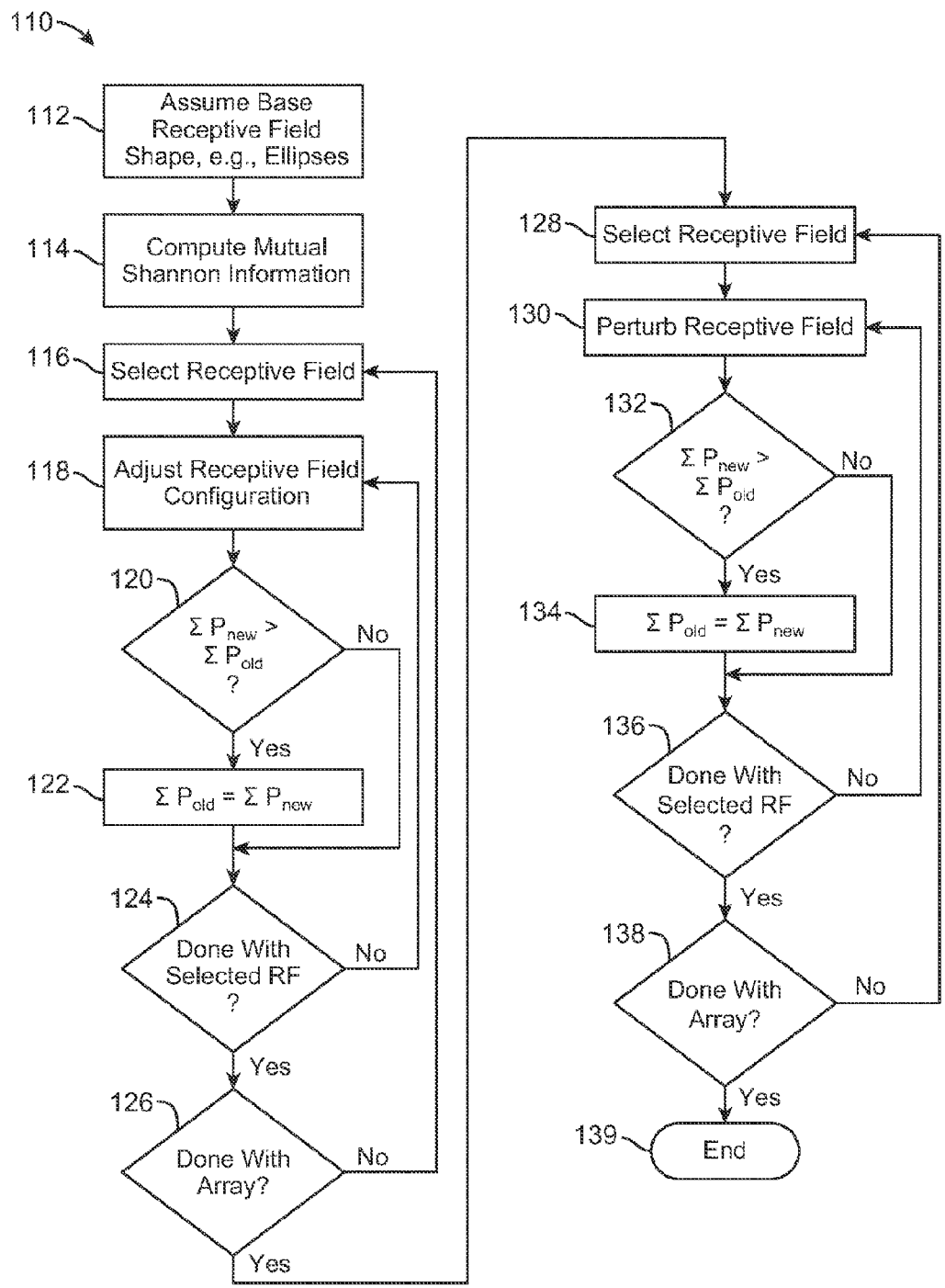
FIG. 10 is a block flow diagram of another portion of the process shown in FIG. 7.
Figure 11:
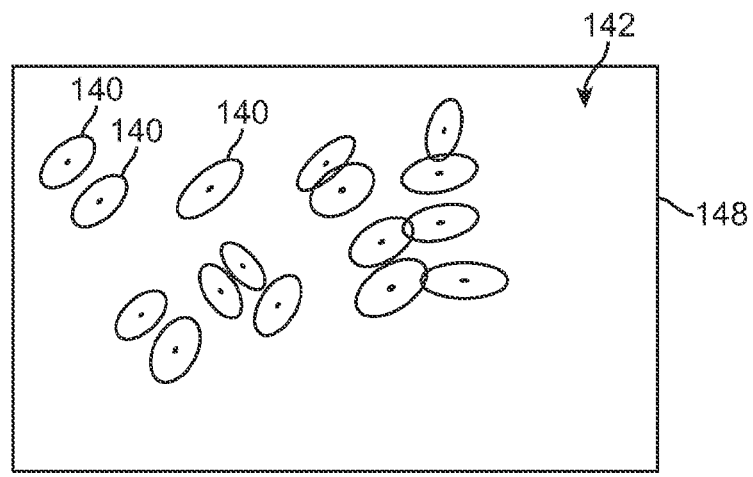
FIG. 11 is a graph of a mosaic of elliptical receptive fields.
Figure 12:
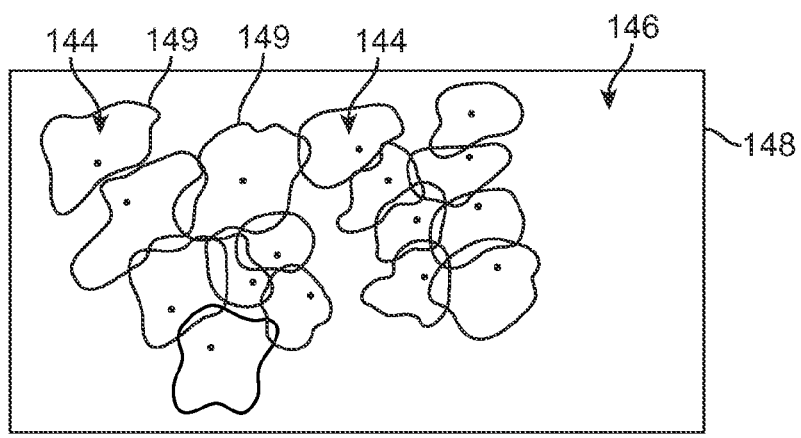
FIG. 12 is a graph of a mosaic of irregularly-shaped receptive fields.

Referring to FIGS. 10-12, with further reference to FIGS. 1-7, the stage 54 of the process 50 comprises a process 110 that includes the stages shown. The process 110 is, however, exemplary only and not limiting, as the process 110 can be altered from the specifics shown and described.

At stage 112, elliptical RFs 140 are assigned to each center point 24 identified by the user 12. The software 86 centers an ellipse 140 at each of the perceived spots of light 24 indicated by the user 12 during the process 60 to form a mosaic 142 (FIG. 11) composed of the ellipses 140. Initially, all RFs 140 have circular shapes (aspect ratio equal to one), and their sizes are set to maximize mutual Shannon information perceived from the spots of light 24 if the spots 24 formed a regular triangular lattice with approximately a 0.7 lattice spacing. This selection is, however, exemplary only and not limiting, as the initial size, aspect ratio and orientation of ellipses could be selected in other ways, e.g., randomly.

At stage 114, mutual information of the mosaic 142 is computed. Using mutual information as an objective function to increase or maximize performance is exemplary only and not limiting in that other measures of performance can be used, such as reducing or minimizing (within practical limitations) the mean square error in reporting the location of visual stimuli. The processor 72 determines the mutual Shannon information, MI, of the mosaic 142, e.g., using the equation $$\sum_{\{r_i\},\{v_j\}} Pr(\{r_i\},\{v_j\})\log_2 \frac{Pr(\{r_i\}|\{v_j\})}{Pr(\{r_i\})},$$

where $r_i$ is the possible electric stimulation of the ith electrode, and $\{v_j\}$ represents the set of possible visual images. For example, different visual images may correspond to different locations of a single light source. In relation to computing the spatial resolution for distinguishing different locations of light sources together with a binary stimulation protocol where each electrode 20 is either stimulated or not stimulated, the calculation of mutual Shannon information can be further simplified as follows.

$$-\Sigma p_i \ln p_i - c\Sigma L_i \qquad (1)$$

Here, $p_i$ represents probabilities of use of different patterns of activation for the electrodes 20. These probabilities are proportional to the area of receptive field i corresponding to a given combination of the stimulated electrodes 20 divided by the total area of the field of view to be encoded of the mosaic 142. The second term in equation (1) takes into account the variability in electrode activation. This variability is the highest near receptive field boundaries. In equation (1), $L_i$ is the circumference of the $i^{th}$ RF 140, whereas c is a constant representing boundary sharpness and has a value, e.g., 0.6 between zero (sharp) and 1 (smooth). When this boundary is broad, then whenever the light falls within the RF boundary, the electrode may or may not be activated, with the probability close to 50%, reducing the amount of mutual information. When the boundary is sharp, for most locations of the light source the $i^{th}$ electrode 140 will either be activated or not be activated, but there will be little uncertainty. Ideally, a mosaic would be used that maximizes the mutual information. As discussed below, the mutual information is preferably maximized within practical constraints, e.g., limited computing power, practical reality of non-infinitesimal incremental changes to characteristics being altered, impracticality of attempting every conceivable RF shape, etc.

At stage 116, one of the RFs 140 is selected for analysis and alteration. The selected RF 140 is considered to be a "center" RF 140 of the mosaic 142.

At stage 118, the configuration of the selected RF 140 is altered. The RF 140 is modified by adjusting a predetermined set of configuration parameters to each of a predetermined set of parameter values. With an elliptical RF, the size, aspect ratio, and orientation are altered. Preferably, the characteristics of size, aspect ratio, and orientation are changed one at a time and incrementally over a range of values for each characteristic.

For example, orientation can be changed over a range 180° using 10 different linearly-spaced values, aspect ratio can be varied from 1 to 1.8 in 0.1 increments, and RF size $\sqrt{ab}$ (a and b are the short and long axes of the ellipse, respectively) can be varied from 0.6 to 0.8 in 0.05 increments. RF size is preferably measured relative to the lattice spacing. After changing one characteristic, the process 110 proceeds to stage 120.

At stage 120, the mutual information of the mosaic 142 is recomputed and compared with the stored, old mutual information. The mutual information in accordance with Eqn. (1) is computed. As the values of $p_i$ for only the selected RF 140 and its neighbors will be different than the previous computation, preferably only the $p_i$'s of the selected RF 140 and its neighbors are computed in order to calculate the mutual information. The $p_i$ of a selected RF 140 and its neighbors may change because RFs 140 overlap, and a $p_i$ of the overlap and a $p_i$ of a non-overlapping portion of the selected RF 140 may both change when the RF 140 is changed. Neighbors to the selected RF 140 are those RFs 140 whose center points 24 are closer to the center point 24 of the selected RF 140 than $L(3^{1/2}+1)/2$ where L is the lattice spacing of the mosaic 142. The lattice spacing can be computed various ways. For example, the mean distance between neighboring percepts 24 can be calculated. As another (often more accurate) example, distances between all percepts 24 (and not just nearest neighbors) are found and a frequency histogram of these distances is computed, and then the triangular lattice of variable lattice spacing and scatter in the lattice positions that can best (e.g., by least squares measure) reproduce the measured histogram is found. If the recomputed mutual information value is not greater than the stored mutual information value, then the process 110 proceeds directly to stage 124. If the recomputed mutual information value is greater than the stored mutual information value, then at stage 122 the recomputed mutual information value is stored as the "old" mutual information value and the present characteristic values are saved, and the process 110 proceeds to stage 124. Thus, if the mutual information increases, the increased mutual information value is stored and the set of characteristics are saved for future use unless a further alteration increases the mutual information more.

At stage 124, an inquiry is made as to whether further adjustments to the characteristics of the selected RF 140 are to be made. If all planned adjustments to the selected RF 140 have been made, then the process 110 proceeds to stage 126 and otherwise returns to stage 118 for the next characteristic adjustment.

At stage 126, an inquiry is made as to whether any RFs 140 remain to be selected and altered. Preferably all of the RFs 140 of the mosaic 142 will be selected, and once all of the RFs 140 have been selected, they will be sequentially selected again until all of the RFs 140 in the entire mosaic 142 have been selected multiple times, here 10 times. If all of the planned selections of the RFs 140 have been made, then the process 110 proceeds to stage 128 and otherwise returns to stage 116 for the next RF 140 selection.

At stage 128, as shown in FIG. 12, an RF 144 of a mosaic 146 of a field of view 148 is selected for further analysis and alteration. Initially, the RFs 144 are the elliptical RFs 140 shown in FIG. 11. As before, the selected RF 144 is considered to be a "center" RF 144 of the mosaic 146.

At stage 130, the configuration of the selected RF 144 is altered to deviate from an ellipse to form the modified mosaic 146. The RFs 144 start from the ellipses, with their corresponding values, determined in stages 116, 118, 122, 124, 126. The shapes of the RFs 144 are preferably altered, resulting in size and orientation alterations. Although numerous possibilities for how to alter the shapes of the RFs 144 are possible, and indeed the type of alteration could be different for different RFs 144, here each of the RFs 144 has its perimeter altered using Legendre polynomials. In particular, the selected RF 144 is altered using a linear combination of Legendre polynomials to describe, in polar coordinates, the distance from the RF center point 24 to its boundary 144 according to:

$$r(\theta) = r_0(\theta) + \sum_{i=1}^{10} A_i P_i(\cos(\theta/2)) \qquad (2)$$

where $r_0(\theta)$ is the ellipse function and $A_i$ is the ith coefficient for Legendre polynomials. Not all of the expansion coefficients A are independent in Eqn. (2). Two of the coefficients $A_i$ are dependent because a boundary condition ($r(0)=r(2\pi)$) was set to ensure closure of the RFs 140. A further condition may be, although it is not required to be, enforced that the center point 24 of each RF 140 is not displaced from its initial position as specified by the user 12. A boundary 149 of the selected RF 140 is modified by adjusting a predetermined set of configuration parameters to each of a predetermined set of parameter values. Here, the coefficients A are adjusted one at a time over a range of values. For example, here the coefficients A are modified linearly in 10 increments over a range of values from −0.1 to 0.1. When a selected coefficient is modified, the process 110 proceeds to stage 132.

At stage 132, the mutual information of the mosaic 146 is recomputed and compared with the stored, old mutual information. For the first comparison, the old mutual information is the mutual information determined using the mosaic 142. The mutual information in accordance with Eqn. (1) is computed for the mosaic 146. As before, as the values of $p_i$ for only the selected RF 144 and its neighbors will be different than the previous computation, preferably only the $p_i$'s of the selected RF 144 and its neighbors are computed in order to calculate the mutual information. Neighbors to the selected RF 144 are those RFs 144 whose center points 24 are closer to the center point 24 of the selected RF 144 than $L(3^{1/2}+1)/2$ where L is the lattice spacing of the mosaic 142. If the recomputed mutual information value is not greater than the stored mutual information value, then the process 110 proceeds directly to stage 136. If the recomputed mutual information value is greater than the stored mutual information value, then at stage 134 the recomputed mutual information value is stored as the "old" mutual information value and the present coefficient values are saved, and the process 110 proceeds to stage 136. Thus, if the mutual information increases, the increased mutual information value is stored and the set of coefficients are saved for future use unless a further alteration increases the mutual information more.

At stage 136, an inquiry is made as to whether further adjustments to the Legendre polynomial coefficients for the selected RF 144 are to be made. If all planned adjustments to the coefficients for the selected RF 144 have been made, then the process 110 proceeds to stage 138 and otherwise returns to stage 130 for the next coefficient adjustment.

At stage 138, an inquiry is made as to whether any RFs 144 remain to be selected and altered. Preferably all of the RFs 144 of the mosaic 146 will be selected, and once all of the RFs 144 have been selected, they will be sequentially selected again until all of the RFs 144 in the entire mosaic 146 have been selected multiple times, here 10 times. If all of the planned selections of the RFs 144 have been made, then the process 110 proceeds to stage 139 where the process 110 ends, and otherwise returns to stage 128 for the next RF 144 selection.

At the end of the process 110, the mosaic 146 is complete. Preferably, as shown, the mosaic 146 spans the entire width and height of field of view 148 of the camera 14 (and beyond, although only the field of view 148 of the camera 14 is shown in FIGS. 11-12). The mosaic, 146 may, however, not completely cover the field of view 148 as there may be small gaps between RFs such that some portions of the field of view 148 do not map to an electrode 20. Alternatively, the mosaic 146 may not span the entire width and/or height of the field of view 148, or at least not the entire height for the entire width and/or the entire width for the entire height (i.e., there may be voids, i.e., regions that are not covered by an RF, at the periphery of the field of view 148). The process 110 preferably reduces, if not minimizes (within practical constraints) the gaps between RFs.

Referring again to FIG. 7, the RFs 144 as determined from stages 128, 130, 132, 134, 136, 138 are programmed into the memory 34 at stage 56. The stored RFs 144 provide a mapping from a field of view of the camera 14 to the electrodes 20 in the array 18.

Figure 13:
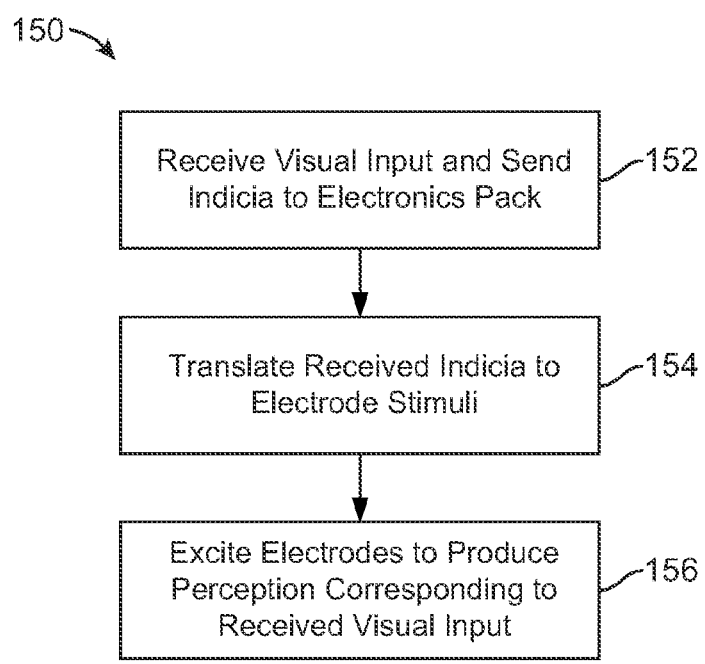
FIG. 13 is a block flow diagram of yet another portion of the process shown in FIG. 7.

Referring to FIG. 13, with further reference to FIGS. 1-7 and 10, the stage 58 of the process 50 comprises a process 150 that includes the stages shown. The process 150 is, however, exemplary only and not limiting, as the process 150 can be altered from the specifics shown and described.

At stage 152, visual input is provided to the system 10. The camera 14 receives optical data, e.g., into a charge-coupled device (CCD) to convert the data from optical to electrical data. The camera 14 transmits electric signals representative of the optical data to the electronics pack 16.

At stage 154, the electronics pack 16 translates the received electric signals representative of the optical information for use by the array 18. The processor 32 operates in accordance with the software 36 to access the stored information about the RFs 144 corresponding to the electrodes 20. The processor 32 converts the electrical data into excitation signals for use by the array 18 to recreate the optical data within the resolution capacity of the array 18. Locations of light detected by the camera 14 are compared to the RFs 144. Signals are produced to cause each electrode 20 whose corresponding RF 144 includes the location of light detected. Thus, if the location falls within only one of the RFs 144, then a signal (or signals) to cause only the single corresponding electrode 20 to be excited will be produced. If the location of detected light falls within multiple RFs 144, i.e., the overlap of two or more RFs 144, then signals to cause all of the corresponding electrodes 20 to be excited will be produced. The pack 16 sends the excitation signals to the array 18.

At stage 156, the electrodes 20 are excited. The array 18 receives the excitation power from the electronics pack 16 and information as to which electrodes 20 to excite. The excitation power is provided to the appropriate electrodes 20 in accordance with the optical data to stimulate the ganglion cells of the user 12 connected to the electrodes 20 to attempt to reproduce the visual data received by the camera 14. The electrodes 20 stimulate the ganglion cells which convey indicia of the stimuli the brain of the user 12, which interprets the indicia to provide the perception of sight.

Other embodiments are within the scope and spirit of the appended claims. For example, due to the nature of software, functions described above can be implemented using non-transitory software, hardware, firmware, hardwiring, or combinations of any of these. Features implementing functions may also be physically located at various positions, including being distributed such that portions of functions are implemented at different physical locations. Further, techniques described above could be used to provide color-specific visual stimuli to help the user 12 see color, e.g., by stimulating appropriate ganglion cells associated with specific colors. The system 10 could be calibrated by having the user 12 indicate not only locations of spots of light perceived, but also the colors perceived. Additionally, other quantities of electrodes in an electrode array may be used than as described above. Further still, electrodes may be stimulated with varying intensities to help convey relative amounts of brightness in optical data received by the camera 14.

Further, while the process 110 described above will likely result in each RF 144 of the mosaic 146 being uniquely shaped, i.e., having a shape different from all other RFs 144 in the mosaic 146, other configurations are possible. For example, a subset of the RFs may be uniquely shaped. Preferably, at least a subset of the RFs will be uniquely shaped, e.g., at least 20, 30, 40, 50 or 60 of the RFs.

Further still, the difference in area between different RFs may be significant. For example, the largest RF area may be at least 10% to 40% larger than the smallest RF area, depending on the scatter in percepts 24.

Also, while the description above focused on retinal implant systems, other systems may be used. For example, the techniques described above may be applied to numerous applications where an irregular set of sensors, e.g., being non-systematically disposed and/or having different receptive field configurations (e.g., shapes, orientations, sizes), is to be stimulated by a regularly-configured array of stimulators, e.g., with stimulators disposed in a uniform lattice. Further, the sensors may not be visual sensors, possibly being aural and/or touch sensors, and/or combinations of these or one or more of these and visual as well.

Further, more than one invention may be disclosed.

Test Data

Figure 14A:
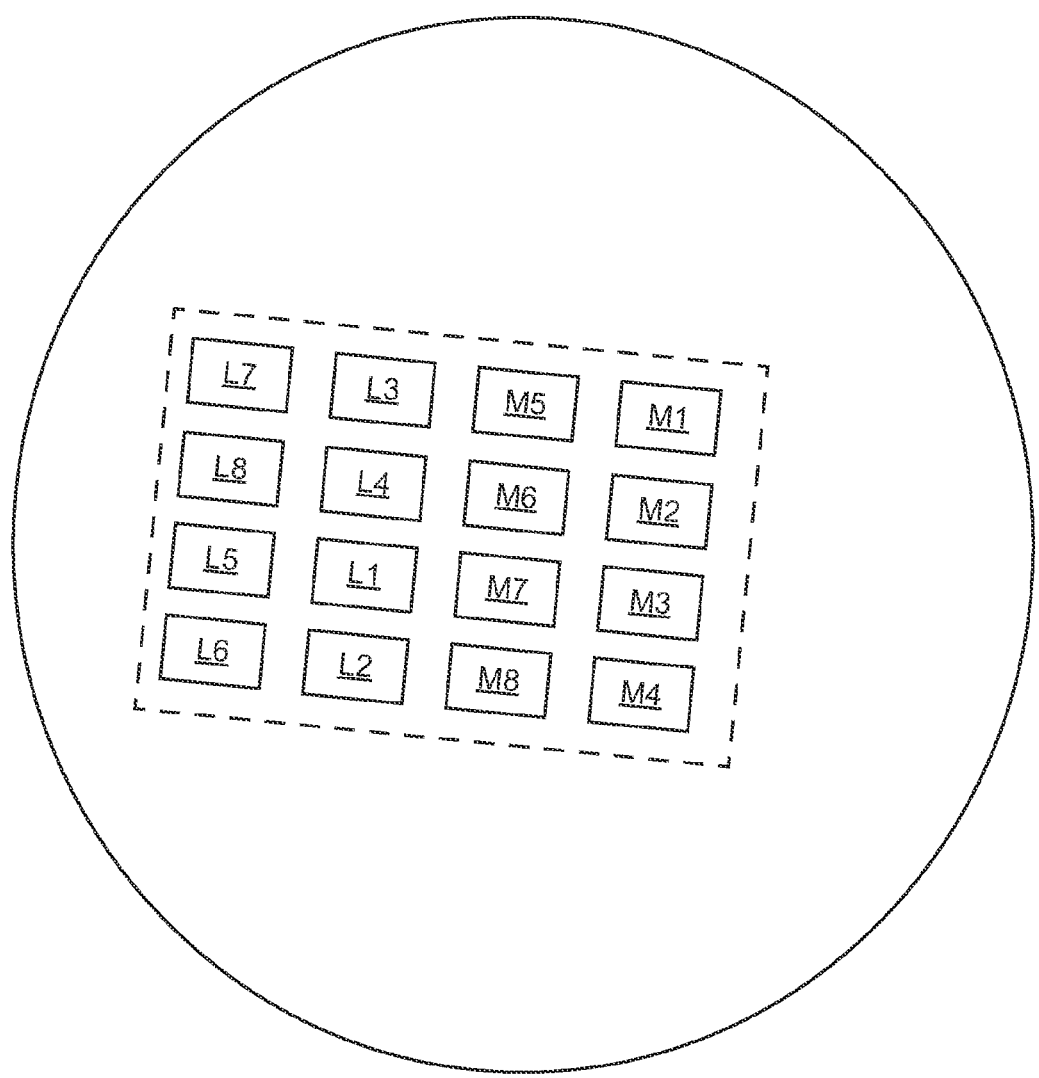
FIG. 14A is a diagram of an implant array disposed on a retina of a person.
Figure 14B:
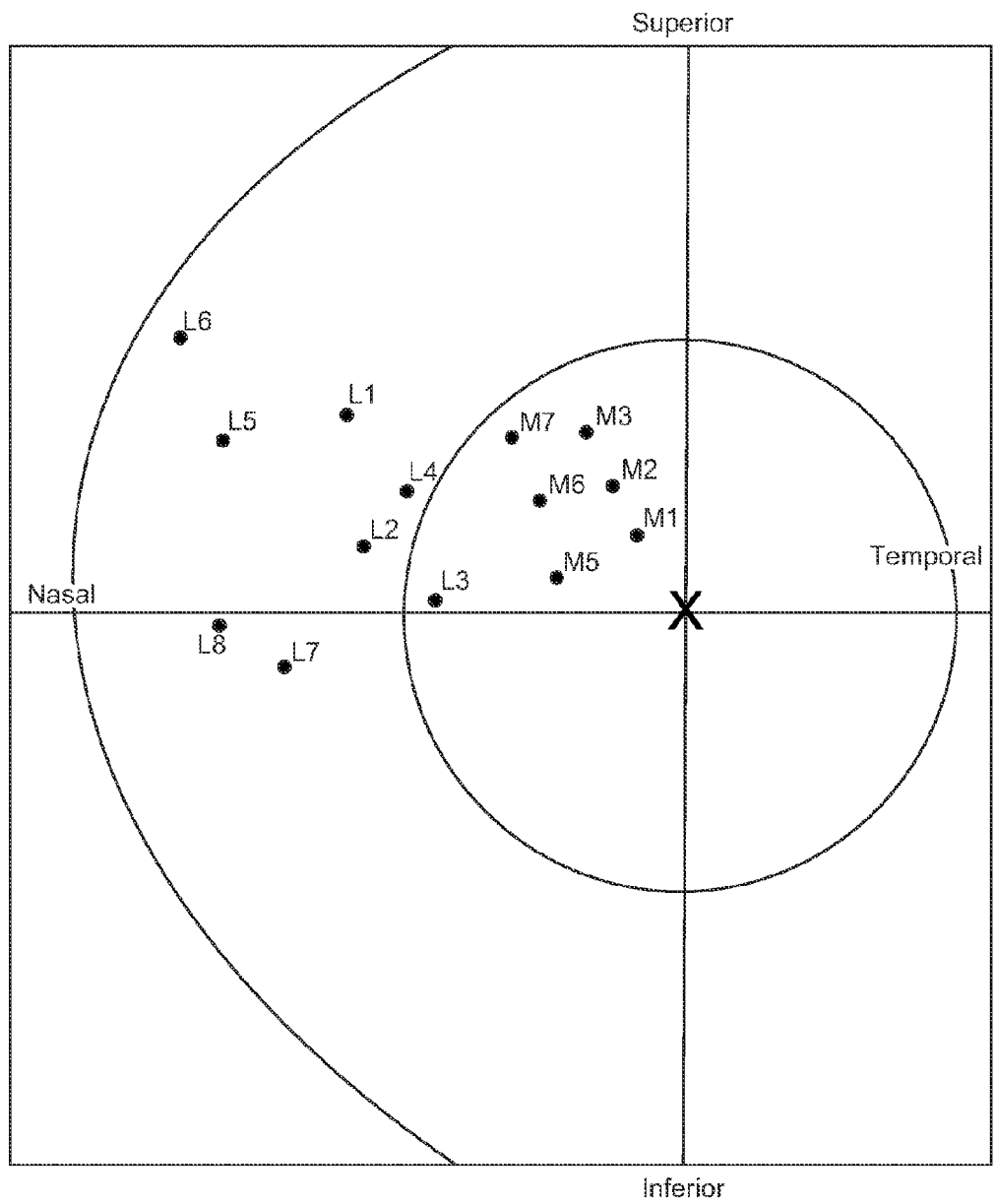
FIG. 14B is a plot of perceived locations of light induced by excitation of the implant array shown in FIG. 14A.

Techniques described above were applied to from Humayun M S, Weiland J D, Fujii G Y, Greenberg R, Williamson R, Little J, Mech B, Cimmarusti V, Van Boemel G, Dagnelie G, de Juan E., "Visual perception in a blind subject with a chronic microelectronic retinal prosthesis." Vision Res 43 (24): 2573-81, 2003 (Humayun). These data were taken from humans implanted with a 16-electrode array. Referring to FIG. 14, although the retina is stimulated according to a regular grid of points shown in FIG. 14A, the perceived locations of spots of light form a highly irregular grid shown in FIG. 14B. For example, the perceived location of light associated with stimulation of an "L2" electrode is grossly out-of-place. Such distortions greatly reduce the spatial resolution of vision provided by the implant, but are different for each patient and cannot be predicted prior to the implantation of the electrode array. However, distortions can be measured by asking patients to report the center positions of visual percepts elicited by the stimulation of individual electrodes.

Figure 15:
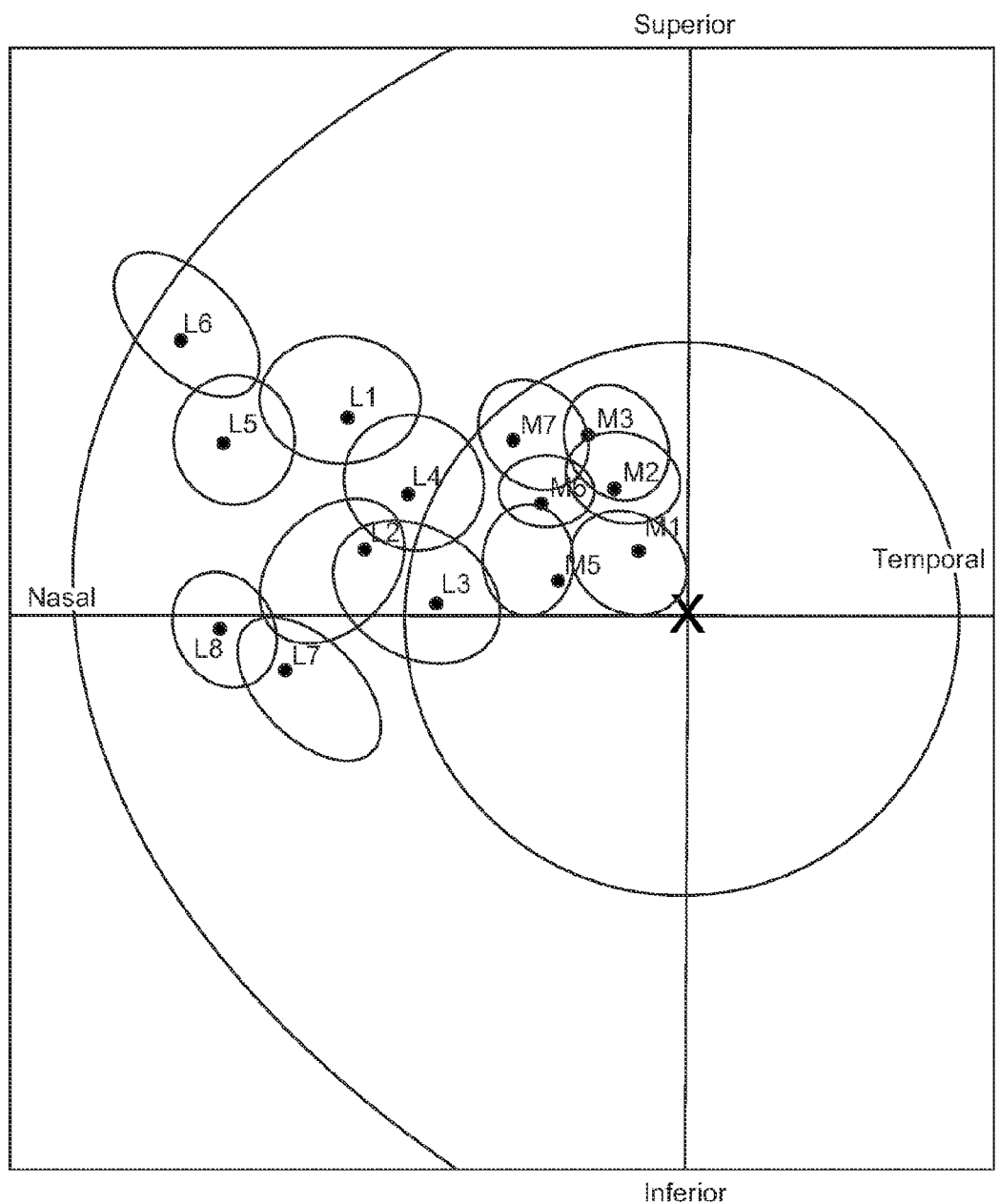
FIG. 15 is a diagram of determined regions of visual space to be associated with stimulations of individual electrodes of the array shown in FIG. 14A for the person providing the data shown in FIG. 14B.

Techniques described above can be used to determine how to encode visual patterns into electrical pulses to compensate for these patient specific irregularities. Results of such compensation are shown in FIG. 15. Ellipses around the perceived locations of spots of light show regions within the visual space where the appearance of contrast should be associated with the stimulation of an individual electrode. For example, a contrast spot appearing anywhere within the part of the visual field bounded by the ellipse centered on an "L6" electrode should be encoded into an electrical pulse of the "L6" electrode. A light flash or contrast variation appearing within the intersection of ellipses centered on "L6" and "L5" electrodes should be associated with stimulation of both of these electrodes. Such a scheme of encoding flashes of light and/or spots of contrast increases the spatial resolution of this particular retinal implant by 20% compared to the encoding of light/contrast that is based on circular response regions drawn around each individual electrode. For example, a patient using this implant and a different encoding scheme could correctly detect whether a spot of light was present in the left or right visual hemi-field, or absent altogether, on about 80% of trials as described in Yanai D, Weiland J D, Mahadevappa M, Greenberg R J, Fine I, Humayun M S, "Visual performance using a retinal prosthesis in three subjects with retinitis pigmentosa." Am J Ophthalmol 143 (5): 820-827, 2007. It is estimated that an effect of the use of techniques discussed above, including using the determined ellipses shown in FIG. 15, is that the number of correct answers to whether a flash of light is present in the left-right visual hemi-fields or absent altogether will increase from 80% to 87.3%. These numbers provide an example of a metric for improvement in the spatial resolution. Another effect is better ability to localize the spot of contrast or a flash of light.

What is claimed is:

1. A method of configuring an apparatus for use in a retinal implant system for a user, the method comprising:
    exciting electrodes of a retinal implant of the retinal implant system, the retinal implant disposed on a retina of the user, the electrodes being excited individually to produce a perception in the user of a spot of light for each electrode;
    prompting the user to provide, and receiving from the user, indicia of perceived locations of the spots of light;
    setting initial receptive fields disposed about the perceived locations, the initial receptive fields forming an initial mosaic; and
    storing mosaic configuration information in the apparatus, the stored mosaic configuration information being indicative of receptive field configurations disposed about the perceived locations and associating each receptive field with locations in a field of view of the user corresponding to the retinal implant.

2. The method of claim 1 further comprising:
    altering configurations of the initial receptive fields to produce a plurality of altered mosaic configurations comprising altered receptive fields; and
    determining mutual information of each of the mosaic configurations;
    wherein storing the mosaic configuration information comprises storing the altered mosaic configuration with a highest mutual information value of the altered mosaic configurations.

3. The method of claim 2 further comprising:
    determining a baseline mutual information value of the initial mosaic with the initial receptive fields;
    determining a new mutual information value for each altered mosaic; and replacing the baseline mutual information value with the new mutual
    information value if the new mutual information value is greater than the baseline mutual information value;
    wherein the storing comprises storing the mosaic configuration information of the altered mosaic configuration corresponding to the baseline mutual information once new mutual information values for all desired altered mosaic configurations have been determined and compared with the baseline mutual information value as of the time when the respective new mutual information values are determined.

4. The method of claim 3 wherein determining the new mutual information comprises calculating areas of only receptive field area portions whose areas change with respect to a previous mosaic configuration, each of the receptive field area portions being associated with a unique set of one or more of the electrodes.

5. The method of claim 2 further comprising repeatedly altering the configuration of each of the altered receptive fields.

6. The method of claim 2 wherein the altering comprises:
    selecting a first receptive field of the initial receptive fields;
    altering the configuration of the first receptive field using each of a first predetermined set of configuration parameter values to produce a first altered receptive field; and
    performing the selecting and altering for a second receptive field of the initial receptive fields, using a second predetermined set of configuration parameter values, after each of the first predetermined set of configuration parameter values have been used to alter the configuration of the first receptive field.

7. The method of claim 6 wherein the selecting and altering are performed for each of the initial receptive fields to determine a set of altered receptive fields.

8. The method of claim 6 further comprising performing the selecting and altering for each of the altered receptive fields of the set of altered receptive fields a predetermined number of times to determine a corresponding predetermined number of sets of altered receptive fields.

9. The method of claim 2 wherein altering configurations of the initial receptive fields to produce a plurality of altered mosaic configurations comprises altering a first receptive field of the initial receptive fields and altering at least a second receptive field adjacent to the first receptive field to produce a first altered mosaic configuration, and wherein determining mutual information of each of the mosaic configurations comprises, for the first altered mosaic configuration:
   determining an altered mutual information contribution of only receptive field area portions whose areas change with respect to a previous mosaic configuration, each of the receptive field area portions being associated with a unique set of one or more of the electrodes; and
   modifying an initial mutual information value of the initial mosaic by replacing an initial mutual information contribution of initial receptive field area portions associated with altered receptive field area portions with the altered mutual information contribution.

10. The method of claim 2 wherein the setting includes setting initial ellipses of particular sizes, aspect ratios, and orientations, and the altering includes changing the sizes, aspect ratios, and orientations of each of the initial ellipses.

11. The method of claim 10 wherein the altering includes changing one of the size, aspect ratio, or orientation of a selected receptive field to form each altered mosaic.

12. The method of claim 10 wherein the altering includes changing a perimeter of a selected receptive field to be different than a perimeter of another of the receptive fields.

13. The method of claim 10 wherein the altering includes changing a perimeter of a selected receptive field in accordance with a Legendre polynomial.

14. The method of claim 13 wherein changing the perimeter of the selected receptive field includes changing coefficients of the Legendre polynomial.

15. The method of claim 2 wherein the setting, storing, altering, and determining are done without receiving user input beyond the indicia of perceived locations of the spots of light, and outside the presence of the user.

16. A computer program product residing on a non-transitory computer-readable medium and comprising computer-readable non-transitory instructions configured to cause a computer to:
   set initial receptive fields disposed about perceived locations, the initial receptive fields forming an initial mosaic, the perceived locations being indicative of locations of perceived light by a user in response to stimulation of portions of a retinal implant disposed on a retina of the user;
   alter configurations of the initial receptive fields to produce a plurality of altered mosaic configurations comprising altered receptive fields;
   determine mutual information of each of the mosaic configurations; and
   store mosaic configuration information, the stored mosaic configuration information being indicative of receptive field configurations disposed about the perceived locations and associating each receptive field with locations in a field of view of the user corresponding to the retinal implant, the stored mosaic configuration information being indicative of the mosaic configuration with a highest mutual information value of the altered mosaic configurations.

17. The computer program product of claim 16 wherein the instructions configured to cause the computer to determine the mutual information are configured to cause the computer to calculate areas of only receptive field area portions whose areas change with respect to a previous mosaic configuration, each of the receptive field area portions being associated with a unique set of one or more of the electrodes.

18. The computer program product of claim 17 wherein the instructions configured to cause the computer to alter configurations are configured to cause the computer to:
   select a first receptive field of the initial receptive fields;
   alter the configuration of the first receptive field using each of a first predetermined set of configuration parameter values to produce a first altered receptive field; and
   select and alter a second receptive field of the initial receptive fields, using a second predetermined set of configuration parameter values, after each of the first predetermined set of configuration parameter values have been used to alter the configuration of the first receptive field.

19. The computer program product of claim 18 wherein the instructions configured to cause the computer to alter configurations of the initial receptive fields to produce a plurality of altered mosaic configurations are configured to cause the computer to alter a first receptive field of the initial receptive fields and altering at least a second receptive field adjacent to the first receptive field to produce a first altered mosaic configuration, and wherein the instructions configured to cause the computer to determine mutual information of each of the mosaic configurations are configured to cause the computer to, for the first altered mosaic configuration:
   determine an altered mutual information contribution of only receptive field area portions whose areas change with respect to a previous mosaic configuration, each of the receptive field area portions being associated with a unique set of one or more of the electrodes; and
   modify an initial mutual information value of the initial mosaic by replacing an initial mutual information contribution of initial receptive field area portions associated with altered receptive field area portions with the altered mutual information contribution.

20. The computer program product of claim 16 wherein the instructions configured to cause the computer to set are configured to cause the computer to set initial ellipses of particular sizes, aspect ratios, and orientations, and the instructions configured to cause the computer to alter are configured to cause the computer to change the sizes, aspect ratios, and orientations of each of the initial ellipses.

21. The computer program product of claim 16 wherein the instructions configured to cause the computer to alter are configured to cause the computer to change one of the size, aspect ratio, or orientation of a selected receptive field to form each altered mosaic.

22. The computer program product of claim 16 wherein the instructions configured to cause the computer to alter are configured to cause the computer to change a perimeter of a selected receptive field to be different than a perimeter of another of the receptive fields.

23. The computer program product of claim 16 wherein the instructions configured to cause the computer to alter are configured to cause the computer to change a perimeter of a selected receptive field in accordance with a Legendre polynomial.

* * * * *